United States Patent [19]
Peiper et al.

[11] Patent Number: 6,007,770
[45] Date of Patent: Dec. 28, 1999

[54] METHOD AND A DEVICE FOR OZONE STERILIZATION OF OBJECTS

[75] Inventors: Uri Peiper, Ramat Hasharon; Gregory Litinsky, Nes Ziona; Yosef Grinshpon, Ramla; Yekutiel Alper, Rishon Lezion, all of Israel

[73] Assignee: State of Israel/Ministry of Agriculture, Israel

[21] Appl. No.: 09/029,491

[22] PCT Filed: Aug. 27, 1996

[86] PCT No.: PCT/IL96/00090

§ 371 Date: Apr. 23, 1998

§ 102(e) Date: Apr. 23, 1998

[87] PCT Pub. No.: WO97/09071

PCT Pub. Date: Mar. 13, 1997

[30] Foreign Application Priority Data

Sep. 1, 1995 [IL] Israel ........................................ 115130

[51] Int. Cl.⁶ ...................................................... A61L 2/00
[52] U.S. Cl. ................................ 422/22; 422/23; 422/25; 422/29
[58] Field of Search .................................. 422/22, 23, 25, 422/29

[56] References Cited

U.S. PATENT DOCUMENTS

| | | | |
|---|---|---|---|
| 4,207,286 | 6/1980 | Gut Boucher | 422/21 |
| 5,200,146 | 4/1993 | Goodman | 422/23 |
| 5,200,158 | 4/1993 | Jacob | 422/22 |
| 5,252,303 | 10/1993 | Goof | 422/292 |
| 5,326,530 | 7/1994 | Bridges | 422/22 |
| 5,393,490 | 2/1995 | Jacob | 422/22 |
| 5,414,324 | 5/1995 | Roth et al. | 315/111.21 |
| 5,876,663 | 3/1999 | Laroussi | 422/23 |

*Primary Examiner*—Krisanne Thornton
*Attorney, Agent, or Firm*—Mayer Brown & Platt

[57] ABSTRACT

The present invention provides a method for sterilization of objects including the steps of placing the object that should be sterilized in a closed vessel; placing the closed vessel between two high voltage electrodes; applying a high voltage between the electrodes and converting the oxygen in the air inside the closed vessel into ozone; and keeping the sterilized object inside the closed vessel as long as needed. A "closed vessel" includes also any form of closed container or any closed plastic bag. The closed vessel may or may not have internal electric conductors. Furthermore, the invention provides a device for ozone sterilization of objects for use in the method. The device for sterilization comprises a sterilization chamber; two parallel high voltage electrodes located inside the chamber and connected to a high voltage transformer; a closed vessel with or without internal electrodes located between the two high voltage electrodes and the object to be sterilized is placed inside the vessel; and two parallel insulators located between the two high voltage electrodes and the closed vessel.

10 Claims, 3 Drawing Sheets

METHOD AND A DEVICE FOR OZONE STERILIZATION OF OBJECTS

FIELD OF THE INVENTION

The present invention relates, in general, to a method and a device for sterilization of objects. More specifically, the present invention relates to a method for ozone sterilization of objects such as plant tissue and tools for laboratories, dentistry, veterinary etc. The present invention further relates to a device for ozone sterilization for use in the said method. The new method, according to the present invention, is based on producing the ozone in a closed and portable vessel or some other package where the sterilized object can be kept till its usage without exposing it to the external atmosphere.

BACKGROUND OF THE INVENTION

Creation and maintenance of aseptic conditions is a very important requirement in many scientific, medical and commercial activities. Sterilization of material, vessels and tools is an important task when these are to be used in biological or medical applications. Today, when the awareness to clean environment and clean work is higher, the importance of clean and sterile tools is a trivial prerequisite when surgical equipments are concerned. Laboratories for medical work or for biological research and development need to work in sterile conditions. Any medical equipment has to be sterilized prior to its use. Dental and hairdressers tools may transfer sources of infection and should therefore be sterilized every time before use. Vessels and tools for tissue culture work have to be sterilized to provide appropriate aseptic environment required for tissue culture applications. The plant tissue itself must also be sterilized before the propagation process can be started. Sterilization of medical tools such as endoscopes and other optical tools for medical examination imposes problems related to effective cleaning of the tools in a short period. The sterilization methods known today include heating, chemical disinfection, UV rays and nuclear radiation. Heating in an autoclave has been the most commonly used procedure because of its availability and application simplicity. However, high temperatures and pressures associated with steam autoclaving place very stringent property specifications on materials for vessels and tools. The sterilization of some materials by heat, particularly plastics, is very limited. Sterilization of devices which include optical and electronic components, which are not "autoclavable" is also problematic. Chemical sterilization techniques are commonly available, but these are usually limited by toxic residues, and require safety precautions for human laborers. Other difficulties that may be encountered with chemicals are special regulations for application and storage of potentially hazardous chemicals. In R&D laboratory work the chemical sterilization can also affect scientific experiments in an adverse way by its residual influence mainly on biological matter. UV and other radiation techniques generally require special instruments that are not commonly available. Nuclear radiation is very effective but it can only be done in special installations. People are often reluctant to use it and it can not be used to sterilize living plant material. Therefore "cold" sterilization techniques with minimal toxicity are highly desirable.

One potential sterilization technology is ozone sterilization. The ozone is a gas produced on site by high voltage gas discharge or by ultraviolet radiation.

Ozone sterilization has become a widely used technique for purification of municipal water systems, particularly from bacteria. The use of ozone generator in swimming pool water treatment is very common. It is also used for sterilization of medical equipment and in the food industry. These commercial applications suggest that ozone sterilization might be viewed as a potential alternative for asepsis purposes. Advantages are simplicity of application, flexibility in operation, minimal toxic residue and relatively low costs. There is no need for raw material which is readily available anywhere and almost no temperature differences are present. It will enable sterilization of a wide range of materials for equipment, tools and growing vessels.

The conventional known technique for atmospheric and surface ozone sterilization is to use a remote, high voltage discharge ozone generator (ozonator) from which ozonized air is directed to a closed vessel holding the substance to be sterilized.

Since ozone is an unstable gas, its concentration is reduced rapidly along its way to the point of application. Thus, in order to get the required concentration at the application point, relatively large ozonators must be used. Larger ozonators require higher electric power and better electric insulation measures. The higher concentration of the ozone at the source calls for more precise sealings. The conventional method is more suitable for large scale sterilization in relatively big chambers where many parts are sterilized together. This conventional method is not very effective in sterilizing surfaces which are not readily exposed to the Ozone. Sterilization of encapsulated objects is not effective at all. After sterilization, the sterilized object has to be removed from the sterilization chamber. By the mere opening of the chamber, new infection may be caused if no special precautions are met.

Another known method is used only in very large volumes by placing the ozone generator inside the large (technological) vessel. In this case, the internal surface and the whole volume are exposed to infection while the generator is being removed. For this reason the method did not become widely used for general purposes.

SUMMARY OF THE INVENTION

The present invention provides a method for sterilization of objects comprising;

(a) placing the object that should be sterilized in a closed vessel; A "closed vessel" includes also any form of closed container or any closed plastic bag. The closed vessel may or may not have internal electric conductors;

(b) placing the closed vessel between to high voltage electrodes;

(c) applying a high voltage between the said electrodes and converting the oxygen in the air inside the closed vessel into ozone;

(d) keeping the sterilized object inside the closed vessel as long as needed.

The embodiment of this invention comprises an electric conductor placed inside the closed vessel (the sterilization vessel or bag).

In some cases as narrow vessels or bags the internal conductor may be unnecessary.

However, in both cases, the ozone is produced within the closed vessel. The electric discharge is produced in the gap between the external electrodes and the neighboring surfaces of the internal electrode, (the preferred position is that they will be parallel to each other).

Furthermore, the said invention provides a device for ozone sterilization of objects for use in the above mentioned method comprising;

a sterilization chamber; two parallel high voltage electrodes located inside the said chamber and connected to a high voltage transformer; a closed vessel with or without internal electrodes located between the two high voltage electrodes and the object to be sterilized is placed inside the said vessel; and two parallel insulators located between the two high voltage electrodes and the closed vessel.

In the preferred embodiment of this device two parallel electric conductors (internal electrodes) are placed in the closed vessel parallel and adjacent to the two external high voltage electrodes, and these two internal electrodes (conductors) are connected to each other by a conductor.

DETAILED DESCRIPTION OF THE INVENTION

The present invention relates to a method and a device for ozone sterilization inside a closed environment. In its preferred embodiment the present invention provides a method and a device for ozone sterilization using an electric conductor (an internal electrode) inside the closed sterilization vessel (hereinafter called the "closed vessel"). The electric discharge occurs in the gap between the external electrodes and the neighboring surfaces of the conductor inside. The electric discharge produces the ozone in the closed chamber from the oxygen contained in the air inside. The efficiency of the process is high due to the fact that the ozone is produced in the same place where it is needed, and need not be transferred. The continuous electric discharge also regenerates the ozone from the oxygen to which it degenerates, being an unstable gas as explained previously. This method will be used to sterilize the internal surfaces of the vessel itself which will be kept closed and aseptic till its usage, and the external surfaces of any material kept inside.

The method and system according to the invention can be used in small and large scale. The closed vessel can be of any size and shape and can be moved and stored including the sterilized material inside. When the closed vessel of the material to be sterilized is small enough, the inside conductor may not be needed. For an example, sterilization of plant material in plastic bags, can be performed in this way. The objective of the method and the device according to the present invention is as follows:
1. To improve the reliability and effectiveness of sterilization.
2. To widen the scope of usage of ozone sterilization.
3. To lower power consumption.
4. To enable production of ozone in a closed vessel which can be kept closed for transportation to the point of usage while keeping sterile conditions inside.
5. To provide a simple relatively cheap and portable device for laboratory and other sterilization purposes.

The new method according to the present invention is based on producing the ozone in a closed and portable vessel or some other package where the sterilized object can be kept till its usage without having to expose it to the external hostile atmosphere.

The new method according to the invention also utilizes the dielectric properties of the package in the high voltage discharge between the electrodes. This may be more effective in sterilizing surfaces where higher concentrations of ozone may be required. It enables sterilization of the inside atmosphere of closed vessels.

The closed vessel, in this case, becomes an inherent part of the generator. The oxygen in the air inside the closed vessel is converted directly into ozone. This opens the possibility for operating small simple devices for use in laboratory and other commercial purposes to sterilize small tools and even plant tissue and keep it closed as long as needed, or in larger enterprises, to sterilize material enclosed in containers on a continuously moving belt.

This method affords considerable flexibilty in establishing dosage levels and in treating objects of various shapes and sizes. Preliminary experiments with plant tissue culture sterilization by ozone using the method and apparatus of the present invention showed advantage over conventional chemical sterilization of the same.

The present invention will be further described and clarified by FIGS. 1, 2 and 3. These figures do not intend to limit the scope of the present invention but to describe the preferred embodiments only.

Figure 1:
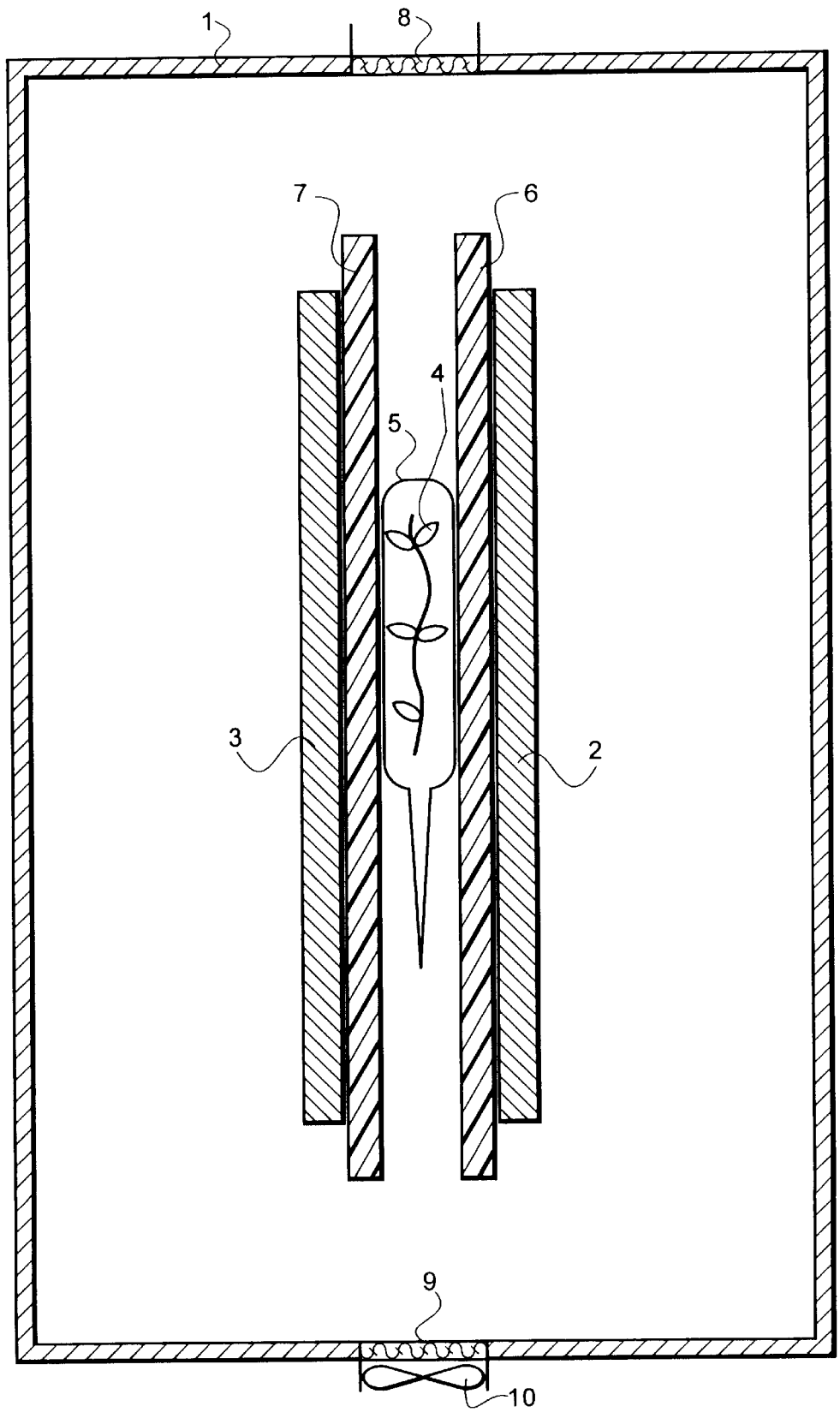
FIG. 1 illustrates a side view of the device, sterilizing plant specimen in a plastic bag without any internal electrode.

FIG. 1 illustrates a device according to the present invention sterilizing plant specimen in a plastic bag. In a sterilization chamber (1) two parallel high voltage electrodes (2) and (3) are located (hereinafter also called the external electrodes). The preferred voltage between these external electrodes during operation is approximately 7–25 KV. A plant specimen (4) is located inside a closed plastic bag (5) (hereinafter also called the closed vessel). This plastic bag is located between the two external electrodes. Two parallel insulators (6) and (7) are placed between the plastic bag (5) and the external electrodes (2) and (3). The sterilization chamber has an inlet filter (8) and an outlet filter (9) and an exhaust fan (10). The closed vessel (the plastic bag) is small and consequently the two external electrodes are adjacent to each other, so we do not need any internal electrode. The sterilization time for plant specimens is about 10, 20 or 30 minutes.

Figure 2:
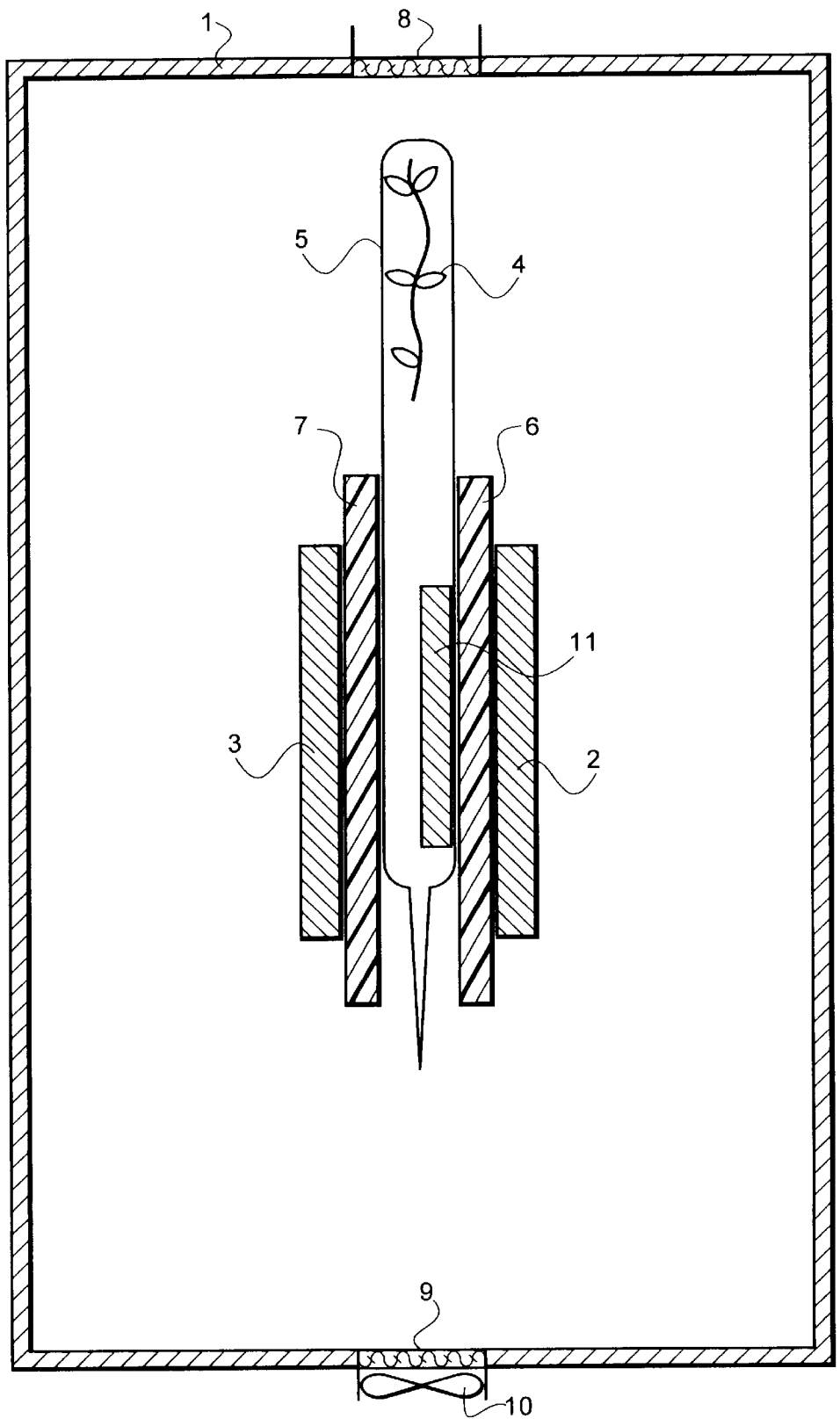
FIG. 2 illustrates a side view of the device, sterilizing plant specimen in a plastic bag with an internal electrode.

FIG. 2 illustrates the same device as described in FIG. 1 but with one main difference. An internal electrode (11) (a conductor) is placed inside the plastic bag. By using this internal electrode the electric spark is "jumping" twice, from one external electrode (3) to the internal electrode (11) and from the internal electrode (11) to the other external one (2).

By using an internal electrode we can reduce the voltage between the two external electrodes. Moreover, we can locate the plant specimen outside the sparking area (as is shown in the figure) and thus the plant does not suffer from any damage.

Figure 3:
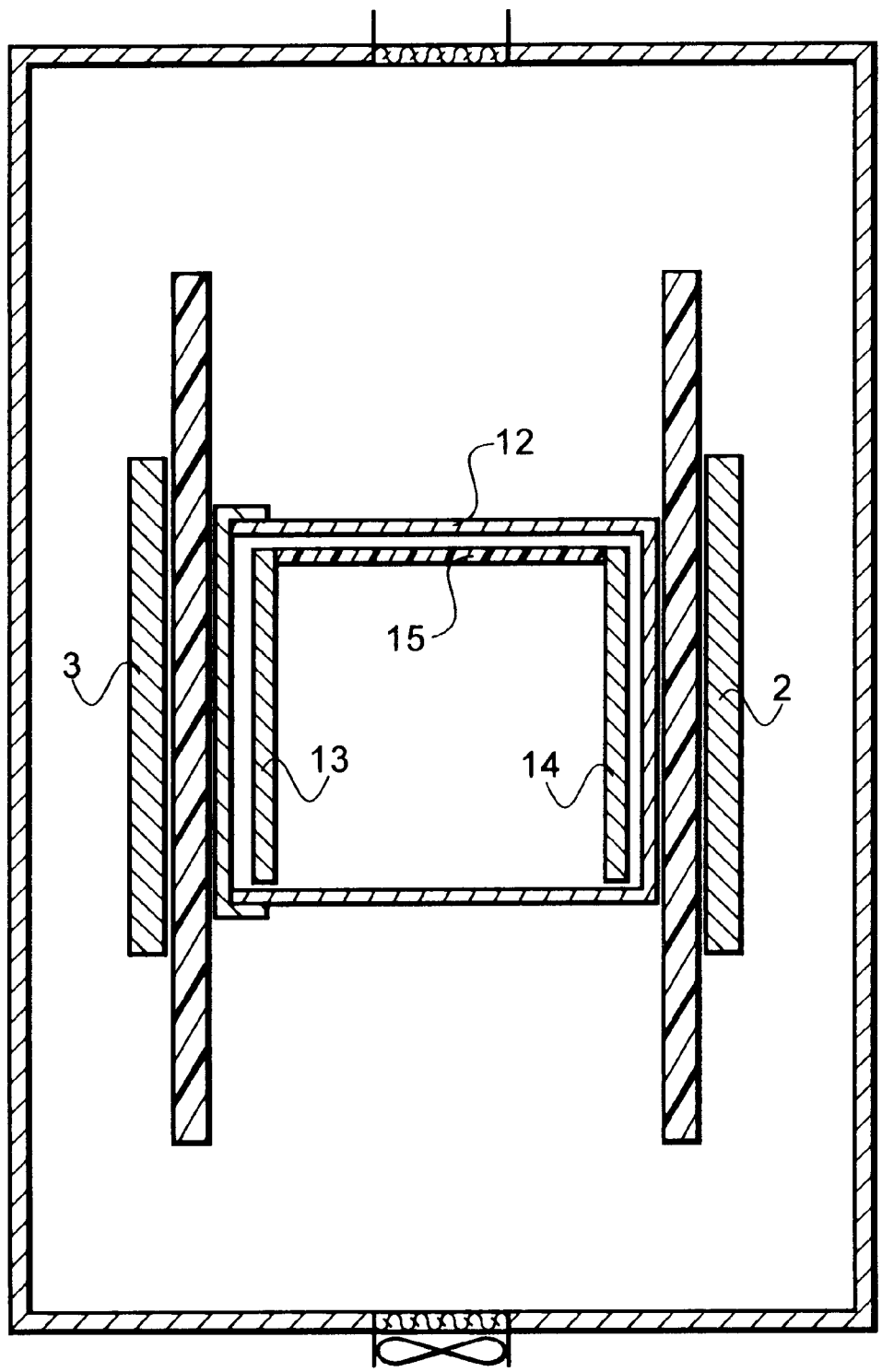
FIG. 3 illustrates a side view of another preferred embodiment of the device having two parallel internal electrodes in the closed vessel connected by a connector.

FIG. 3 illustrates a side view of another preferred embodiment of the invention. This device is the same as described in FIGS. 1 and 2 except the closed vessel (12).

The closed vessel has two parallel upper (13) and lower (14) internal electrodes (conductors) connected to each other by galvonic connector (15) (conductor). During the ozonation the sparks are taking place between the upper external high voltage electrode and the adjacent parallel internal electrode, and between the lower internal electrode and the external lower electrode. This ozonator as described in FIG. 3 can use a closed vessel having any size and shape because the problem of the distance between the two external electrodes does not exist anymore.

We claim:

1. A method for sterilization of objects comprising:
   placing the object that should be sterilized in a closed vessel;

placing the closed vessel between two high voltage electrodes;

applying a high voltage between the said electrodes and converting the oxygen in the air inside the closed vessel into an ozone; and keeping the sterilized object inside the closed vessel as long as needed.

2. A method for sterilization of objects according to claim 1 wherein at least one electric conductor is placed inside the closed vessel.

3. A method according to claim 1 wherein the objects to be sterilized are tools for laboratories, medicine, dentistry and veterinary or plant tissues.

4. A device for ozone sterilization of objects comprising: a sterilization chamber; two parallel high voltage electrodes located inside the said chamber connected to a high voltage transformer; a closed vessel located between the two high voltage electrodes and the object to be sterilized is located in the said vessel; and two parallel insulators located between the two high voltage electrodes and the closed vessel.

5. A device for ozone sterilization according to claim 4 wherein at least one electric conductor is placed in the closed vessel.

6. A device for ozone sterilization according to claim 5 wherein two electric conductors are connected to each other by any connector and the object to be sterilized is located in the closed vessel.

7. A device according to claim 4 wherein the sterilization chamber has at least one filter.

8. A device according to claim 4 wherein the closed vessel is a plastic bag.

9. A device according to claim 7 wherein the object to be sterilized inside the plastic bag is selected from the group consisting of a plant specimen and a tissue.

10. A method for sterilization of objects according to claim 1 wherein the closed vessel has internal electric conductors.

* * * * *